(12) United States Patent
Martinez et al.

(10) Patent No.: US 11,504,546 B2
(45) Date of Patent: Nov. 22, 2022

(54) NEEDLE GUIDANCE DEVICE FOR BRACHYTHERAPY AND METHOD OF USE

(71) Applicant: COWLES VENTURES, LLC, Spokane, WA (US)

(72) Inventors: Alvaro Martinez, Mercer Island, WA (US); Mary Ann Slavik, Mercer Island, WA (US); Emily Lin, Mercer Island, WA (US)

(73) Assignee: COWLES VENTURES, LLC, Spokane, WA (US)

( * ) Notice: Subject to any disclaimer, the term of this patent is extended or adjusted under 35 U.S.C. 154(b) by 0 days.

(21) Appl. No.: 16/801,103

(22) Filed: Feb. 25, 2020

(65) Prior Publication Data

US 2020/0276451 A1    Sep. 3, 2020

Related U.S. Application Data

(60) Provisional application No. 62/812,197, filed on Feb. 28, 2019.

(51) Int. Cl.
*A61N 5/10* (2006.01)

(52) U.S. Cl.
CPC .......... *A61N 5/1007* (2013.01); *A61N 5/103* (2013.01); *A61N 2005/1009* (2013.01); *A61N 2005/1012* (2013.01); *A61N 2005/1024* (2013.01); *A61N 2005/1025* (2013.01)

(58) Field of Classification Search
CPC .......................................... A61N 5/1001–1027
See application file for complete search history.

(56) References Cited

U.S. PATENT DOCUMENTS

| | | |
|---|---|---|
| 3,351,049 A | 11/1967 | Lawrence |
| 3,566,125 A | 2/1971 | Linhart, Jr. et al. |
| 4,323,055 A | 4/1982 | Kubiatowicz |
| 4,349,033 A | 9/1982 | Eden |
| 4,401,124 A | 8/1983 | Guess et al. |
| 4,509,506 A | 4/1985 | Windorski et al. |

(Continued)

FOREIGN PATENT DOCUMENTS

| | | |
|---|---|---|
| CN | 101198287 A | 6/2008 |
| EP | 0292630 A1 | 11/1988 |

(Continued)

OTHER PUBLICATIONS

Pignol, M.D., "First Report of a Permanent Breast PD Seed Implant as Adjuvant Radiation Treatment for Early-Stage Breast Cancer"—Clinical Investigation 2006, 6 pages.

(Continued)

*Primary Examiner* — Thaddeus B Cox
(74) *Attorney, Agent, or Firm* — Manatt, Phelps & Phillips, LLP (57) ABSTRACT

A brachytherapy needle guidance device is a device that facilitates the placement of a brachytherapy needle into a treatment region in tissue. This tissue may a breast tissue and the brachytherapy needle may be a fiducial needle. The brachytherapy needle guidance device may have an anchoring feature that anchors the brachytherapy needle guidance device into the tissue once it is properly positioned. The brachytherapy needle guidance device is used by software for treatment planning.

17 Claims, 4 Drawing Sheets

(56) References Cited

U.S. PATENT DOCUMENTS

| | | |
|---|---|---|
| 4,702,228 A | 10/1987 | Russell, Jr. et al. |
| 4,704,774 A | 11/1987 | Fujii et al. |
| 4,763,642 A | 8/1988 | Horowitz |
| 4,763,643 A | 8/1988 | Vrzalik |
| 4,805,628 A | 2/1989 | Fry et al. |
| 4,815,449 A | 3/1989 | Horowitz |
| 4,869,259 A | 9/1989 | Elkins |
| 4,977,897 A | 12/1990 | Hurwitz |
| 4,994,013 A | 2/1991 | Suthanthiran et al. |
| 4,995,396 A | 2/1991 | Inaba et al. |
| 5,014,708 A | 5/1991 | Hayashi et al. |
| 5,061,275 A | 10/1991 | Wallsten et al. |
| 5,076,278 A | 12/1991 | Vilkomerson et al. |
| 5,081,997 A | 1/1992 | Bosley, Jr. et al. |
| 5,163,896 A | 11/1992 | Suthanthiran et al. |
| 5,201,314 A | 4/1993 | Bosley et al. |
| 5,289,831 A | 3/1994 | Bosley |
| 5,327,891 A | 7/1994 | Rammler |
| 5,342,283 A | 8/1994 | Good |
| 5,460,592 A | 10/1995 | Langton et al. |
| 5,490,521 A | 2/1996 | Davis et al. |
| 5,503,614 A | 4/1996 | Liprie |
| 4,954,126 A | 5/1996 | Wallsten |
| 4,655,771 A | 9/1996 | Wallsten |
| 5,611,870 A | 3/1997 | Horne et al. |
| 5,622,687 A | 4/1997 | Krishnan et al. |
| 5,713,828 A | 2/1998 | Coniglione |
| 5,759,154 A | 6/1998 | Hoyns et al. |
| 5,766,135 A | 6/1998 | Terwilliger |
| 5,769,795 A | 6/1998 | Terwilliger |
| 5,808,020 A | 9/1998 | Ferrieri et al. |
| 5,820,549 A | 10/1998 | Marian, Jr. |
| 5,820,554 A | 10/1998 | Davis et al. |
| 5,821,541 A | 10/1998 | Turner |
| 5,833,593 A | 11/1998 | Liprie |
| 5,857,956 A | 1/1999 | Liprie |
| 5,861,226 A | 1/1999 | Home et al. |
| 5,921,933 A | 7/1999 | Sarkis et al. |
| 5,924,973 A | 7/1999 | Weinberger |
| 5,961,527 A | 10/1999 | Whitmore et al. |
| 5,961,529 A | 10/1999 | Arnold |
| 5,976,067 A | 11/1999 | Tucker et al. |
| 5,989,265 A | 11/1999 | Bouquet De La Joliniere et al. |
| 5,997,463 A | 12/1999 | Cutrer |
| 6,007,475 A | 12/1999 | Slater et al. |
| 6,010,445 A | 1/2000 | Armini et al. |
| 6,018,676 A | 1/2000 | Davis et al. |
| 6,030,333 A | 2/2000 | Sioshansi et al. |
| 6,045,495 A | 4/2000 | Weinberger |
| 6,045,775 A | 4/2000 | Ericcson et al. |
| 6,059,714 A | 5/2000 | Armini et al. |
| 6,060,036 A | 5/2000 | Armini |
| 6,060,040 A | 5/2000 | Tournier et al. |
| 6,066,083 A | 5/2000 | Slater et al. |
| 6,074,337 A | 6/2000 | Tucker et al. |
| 6,080,099 A | 6/2000 | Slater et al. |
| 6,086,942 A | 7/2000 | Carden, Jr. et al. |
| 6,095,967 A | 8/2000 | Black et al. |
| 6,099,457 A | 8/2000 | Good |
| 6,099,458 A | 8/2000 | Robertson |
| 6,103,295 A | 8/2000 | Chan et al. |
| 6,106,454 A | 8/2000 | Berg et al. |
| 6,106,473 A | 8/2000 | Violante et al. |
| 6,120,856 A | 9/2000 | Liberti et al. |
| 6,123,920 A | 9/2000 | Gunther et al. |
| 6,132,359 A | 10/2000 | Bolenbaugh |
| 6,132,677 A | 10/2000 | Ohriner |
| 6,139,819 A | 10/2000 | Unger et al. |
| 6,146,322 A | 11/2000 | Papirov et al. |
| 6,146,615 A | 11/2000 | Davies et al. |
| 6,159,142 A | 12/2000 | Alt |
| 6,174,330 B1 | 1/2001 | Stinson |
| 6,200,255 B1 | 3/2001 | Yu |
| 6,242,742 B1 | 6/2001 | Geay et al. |
| 6,242,743 B1 | 6/2001 | DeVito et al. |
| 6,347,443 B2 | 2/2002 | Coniglione |
| 6,364,855 B1 | 4/2002 | Zappala |
| 6,398,709 B1 | 6/2002 | Ehr et al. |
| 6,405,733 B1 | 6/2002 | Fogarty et al. |
| 6,508,786 B2 | 1/2003 | Huitema et al. |
| 6,547,782 B1 | 4/2003 | Taylor |
| 6,549,802 B1 | 4/2003 | Thornton |
| 6,572,525 B1 | 6/2003 | Yoshizumi |
| 6,579,262 B1 | 6/2003 | Mick et al. |
| 6,585,633 B2 | 7/2003 | Vitali et al. |
| 6,621,086 B1 | 9/2003 | Appleby |
| 6,648,811 B2 | 11/2003 | Sierocuk et al. |
| 6,723,052 B2 | 4/2004 | Mills |
| 6,752,753 B1 | 6/2004 | Hoskins et al. |
| 6,846,282 B1 | 1/2005 | Ford |
| 8,560,052 B2 | 10/2013 | Mills |
| 8,764,619 B2 | 7/2014 | Pitman |
| 10,449,387 B2 | 10/2019 | Pitman |
| 10,456,592 B2 | 10/2019 | Pitman |
| 2002/0022781 A1 | 2/2002 | McIntire et al. |
| 2002/0183581 A1 | 12/2002 | Yoe et al. |
| 2004/0034312 A1* | 2/2004 | Koster ............... A61N 5/1027 600/585 |
| 2004/0059177 A1* | 3/2004 | Baltas ............... A61N 5/1007 600/3 |
| 2004/0116767 A1 | 6/2004 | Lebovic et al. |
| 2005/0049490 A1 | 3/2005 | Mills |
| 2005/0070753 A1 | 3/2005 | Forman et al. |
| 2006/0100475 A1 | 5/2006 | White et al. |
| 2006/0122452 A1 | 6/2006 | Hooft |
| 2007/0021642 A1 | 1/2007 | Lamoureux et al. |
| 2007/0043291 A1 | 2/2007 | Fidel et al. |
| 2007/0049786 A1 | 3/2007 | Edmundson |
| 2007/0142695 A1 | 6/2007 | White et al. |
| 2007/0167749 A1 | 7/2007 | Yarnall et al. |
| 2007/0265486 A1 | 11/2007 | Van 't Hooft |
| 2007/0265487 A1 | 11/2007 | Lamoureux et al. |
| 2008/0086026 A1 | 4/2008 | Keppel et al. |
| 2009/0099402 A1 | 4/2009 | Lamoureux et al. |
| 2009/0198094 A1* | 8/2009 | Fenster ............... A61B 8/0841 600/3 |
| 2009/0228001 A1 | 9/2009 | Pacey |
| 2009/0264696 A1 | 10/2009 | White et al. |
| 2009/0326314 A1 | 12/2009 | Cutrer et al. |
| 2010/0036245 A1 | 2/2010 | Yu et al. |
| 2010/0152519 A1 | 6/2010 | White et al. |
| 2010/0268014 A1* | 10/2010 | Pitman ............... A61N 5/1015 600/7 |
| 2011/0004094 A1 | 1/2011 | Stubbs et al. |
| 2012/0189551 A1* | 7/2012 | Frank ............... A61K 49/10 424/9.36 |
| 2012/0323117 A1 | 12/2012 | Neustadter et al. |
| 2013/0289389 A1 | 10/2013 | Hermann et al. |
| 2013/0289390 A1 | 10/2013 | Hermann et al. |
| 2014/0275984 A1 | 9/2014 | Hermann et al. |
| 2016/0022415 A1 | 1/2016 | Lebovic et al. |
| 2016/0051839 A1 | 2/2016 | Greskovich, Jr. et al. |
| 2016/0166328 A1* | 6/2016 | De Vries ............... A61B 90/30 600/7 |
| 2017/0151033 A1 | 6/2017 | Faure |
| 2017/0181842 A1 | 6/2017 | Lebovic et al. |
| 2017/0181843 A1 | 6/2017 | Lebovic et al. |
| 2017/0296842 A1 | 10/2017 | Helle et al. |
| 2019/0336274 A1 | 11/2019 | Lebovic et al. |
| 2020/0276455 A1 | 9/2020 | Martinez et al. |
| 2020/0289845 A1 | 9/2020 | Martinez et al. |

FOREIGN PATENT DOCUMENTS

| | | |
|---|---|---|
| JP | 2014504603 A | 2/2014 |
| KR | 20170037097 A | 4/2017 |
| WO | WO9533512 A1 | 12/1995 |
| WO | WO9640352 A1 | 12/1996 |
| WO | WO9717104 A1 | 5/1997 |
| WO | WO9719706 A1 | 6/1997 |
| WO | WO9719724 A1 | 6/1997 |
| WO | WO9801186 A1 | 1/1998 |
| WO | WO9940970 A1 | 8/1999 |

(56) References Cited

FOREIGN PATENT DOCUMENTS

| WO | WO0009211 A1 | 2/2000 |
| WO | WO0172202 A2 | 10/2001 |
| WO | WO2004014215 A2 | 2/2004 |
| WO | WO2007134103 A2 | 11/2007 |
| WO | WO2012100206 A2 | 7/2012 |

OTHER PUBLICATIONS

Cross MJ, et al. Impact of a Novel Bioabsorbable Implant on Radiation Treatment Planning for Breast Cancer. World J Surg. Feb. 2017, vol. 41, Issue 2, pp. 464-471.Published online Oct. 5, 2016 (Year: 2016).

Brown, Design Considerations for Piezoelectric Polymer Ultrasound Transducers, IEEE Trans on Ultrasonics, Ferro-electrics, and Frequency Control, vol. 47, No. 6, Nov. 2000, p. 1377-1396.

Dicker AP, Lin CC, Leeper DB, Waterman FM; "Isotope selection for permanent prostate implants? An evaluation of 103 Pd versus 1251 based on radiobiological effectiveness and dosimetry," Seminars in Urologic Oncology, May 2000, 18(2):152-159. https://www.ncbi.nlm.nih.gov/pubmed/10875458.

* cited by examiner

NEEDLE GUIDANCE DEVICE FOR BRACHYTHERAPY AND METHOD OF USE

RELATED APPLICATIONS

This application claims the benefit of U.S. Provisional Application No. 62/812,197, filed Feb. 28, 2019, and which is incorporated herein by reference.

FIELD

The disclosure relates generally to a mechanism and method for radiation oncology.

BACKGROUND

When women are treated for breast cancer (which is the most commonly diagnosed cancer in women), they can opt for a mastectomy (complete removal of the breast tissue) or a breast conservation surgery. Due to the use of widespread screening mammograms, women are diagnosed with localized and early-stage disease so that the breast conservation surgery followed by radiation treatment may be used. The typical radiation treatment is adjuvant breast radiation. While the adjuvant breast radiation results in good survival rates, adjuvant breast radiation treatment typically takes 3.5 to 7 weeks which is too long. In addition, since the adjuvant breast radiation treatment is typically provided using external beam radiation, there is a greater risk of acute skin reactions due to the healthy tissue interaction with the radiation.

As a result, accelerated partial breast irradiation may be used which results in a quicker treatment time and less radiation-induced acute skin reactions. One technique used for the accelerated partial breast irradiation is brachytherapy. In one method, radioactive sources are permanently implanted into the breast tissue at the site of the surgery wherein the radioactive sources may be high dose or low dose.

Currently there are a handful of ways to insert radioactive sources into breast tissue. One is by a free hand method, another uses a compressive template device to temporary hold insertion catheters and the last uses a locking template system and non-fixated fiducial needle. These methods are limited in that they do not ensure the sources are placed in the desired location as prescribed by the treatment plan 100% of the time. The lack of ability to place the radioactive sources in the desired location means that the remaining tumor margin is not receiving the appropriate radiation and healthy tissue is receiving unwanted radiation.

In the high dose rate brachytherapy area, a clinician would place hollow catheters into the breast to facilitate the insertion of a temporary radioactive source per a treatment plan which are then removed once the treatment is completed. The placement of these catheters may be by either free hand directly into the breast or by free hand though compressive template systems used to stereo-tactically immobilize the breast. Both Varian Medical Systems and Nucletron offer commercially available template immobilization products.

In the low dose rate brachytherapy area, one method for permanent breast radioactive seed implantation is described in detail in "First Report of a Permanent Breast103PD Seed Implant As Adjuvant Radiation Treatment for Early-Stage Breast Cancer", Dr. Jean-Philippe Pignol et al., International Journal of Radiation Oncology Biological Physics, Vol. 64, No. 1, pp. 176-181 (2006) which is incorporated herein by reference. This method uses a non-fixated fiducial needle, locking template and stereotactic fixation to insert lose dose rate (LDR) radioactive source strands into the treatment site. In this method, the fiducial needle can be challenging to place in the surgical cavity because locating the surgical cavity relies on the user's ultrasound skills. Also, the fiducial needle can migrate/move once inserted thus changing the depth at which the source strands are deployed. In addition, the system is very cumbersome to use and is not user intuitive. The user manually operates the locking template and stereotactic fixation system by turning knobs to adjust and lock/unlock positions. The position and orientation of the locking template is determined by a treatment planning software. The correct position and orientation of the template are verified by other instruments such as an inclinometer and a ruler. Overall, the system can be difficult to use in a reproducible and precise manner.

Thus, it is desirable to provide a needle guidance device that can mark the treatment area with the goal of improving the reproducibility of the procedure and ensuring that the sources are reliably and consistently inserted in an exact position per a patient prescription treatment plan from patient to patient as well as improve the ease-of-use of the device and procedure and it is to this end that the disclosure is directed.

DETAILED DESCRIPTION OF ONE OR MORE EMBODIMENTS

It is noted that the following disclosure is particularly applicable to radioactive source implantation into breast tissue and it is in this context that the disclosure will be described with an example. It will be appreciated, however, that the device and method has greater utility since the device can be used with other devices besides the template, needles, and radioactive sources and in various different tissues in which it would be desirable to be able to perform brachytherapy using radioactive seeds. Furthermore, although the example below illustrates a fiducial needle being guided into breast tissue, the device also may be used to guide other brachytherapy devices into the tissue.

Figure 1:
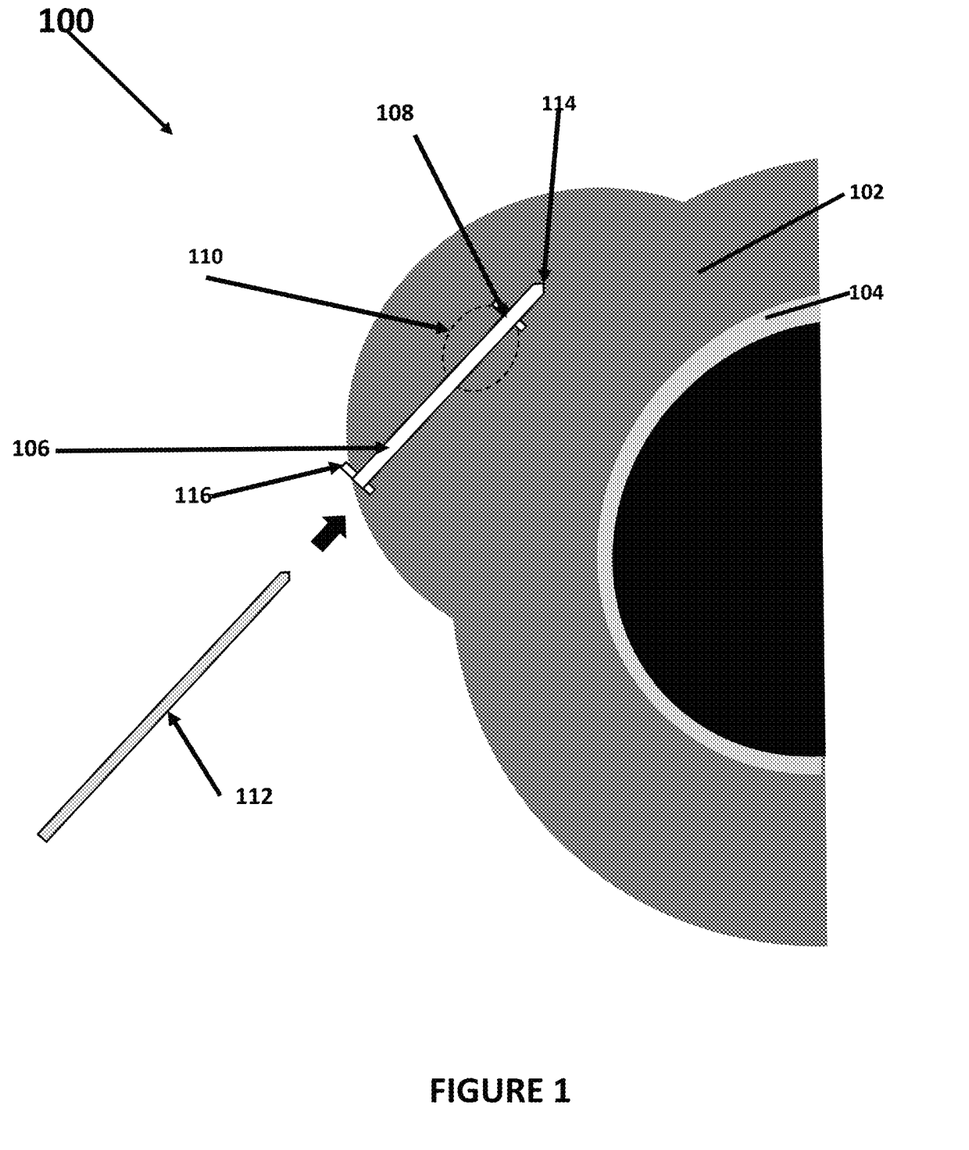
FIG. 1 is a caudal cross section of breast tissue and an example of the needle guidance device used with a fiducial needle.

FIG. 1 is a caudal cross section of breast tissue and an example of the needle guidance device 100 used with a fiducial needle to guide one or more fiducial needles 112 to a treatment region 110 within tissue. In the example shown in FIG. 1, the tissue is breast tissue 102 shown against a chest wall 104 of a patient that has the treatment region. Once the one or more fiducial needles are fixed into a region of treatment 110, one or more radioactive seeds or strands of seeds may be placed into the tissue (based on a treatment plan) to irradiate a tumor in the tissue or irradiate a margin from which a tumor has been removed by the radiation released by the one or more radioactive seeds. As noted above, the needle guidance device 100 may be used to guide a needle into various different tissues and is not in any way limited to the example use in breast tissue shown in FIG. 1.

A needle guidance device 106 may be inserted into and secured in the tissue. The needle guidance device may have a body portion that can attach onto or take in a needle, such as the exemplary fiducial needle 112 shown in FIG. 1. Example of the needle guidance device 106 and its body portion may include, for example, a hollow tube, such as a catheter or cannula, through which a needle can be inserted (as shown in the example in FIG. 1), a guidewire that can be used with a hollow needle, a balloon catheter, through which a needle can be inserted and/or a balloon on a guidewire. The needle guidance device 106 may have an anchoring feature 108 that secures the device 106 into the tissue, but is easily removable. Examples of the anchoring feature 108 may include, for example, holes for suturing the device 106 into the tissue as shown in the example in FIG. 1, one or more hooks can be deployed into the tissue as in the example embodiment shown in FIG. 3, a screw-like tip (tip has threads) can be used to secure the device 106 into tissue and/or a balloon can be inflated inside the cavity to secure the device 106.

The device 106 may be manufactured out of a polymer-based material, stainless steel, stainless steel alloys, bioabsorbable materials or any other suitable material. The device 106 may have a feature 114 that allows the device 106 to be placed percutaneously into the cavity (for example, formed when a tumor has been surgically removed) in the treatment region 110. The feature 114 may be, for example, a sharpened tip (such as shown in the examples in FIGS. 1 and 3) to facilitate easy penetration into tissue or an accessory component such as a trochar can be used to place the device 106 into the tissue. The device 106 or at least one portion of the device 106 may be visible under one or more imaging modalities (e.g., fluoroscopy, magnetic resonance imaging, computerized tomography, ultrasound, etc.). For example, the entire body of the device 106 may be visible, features on or inside the device (i.e., beads, bands, markers, imaging agent) may be visible, balloon can be inflated for visibility and/or an accessory component that is visible under medical imaging can be placed inside the device wherein the accessory component may have features for depth measurements.

The device 106 may also have an interface feature 116 at an end of the body portion at each end of the body portion that includes the anchoring feature so that the device 106 can accept and interface with one or more brachytherapy devices, including a needle. For example, an end of the device 106 may have a flared opening to ease the insertion of a fiducial device, such as a needle and/or may have a cap can be attached to the end of the device, on the skin surface, with an accessible opening for a fiducial device, such as a needle, to enter the device as shown in the example in FIG. 1. The device 106 may contain electronic components, such as sensors, that can communicate or interact with software. For example, the location of the device 106 can be identified with software and the treatment plan can be adjusted according to the location of the device 106. In addition, the device 106 can be used with an ultrasound imaging system to provide real-time location of the insertion and guidance at the time the device is implanted which provides visualization of the surrounding tissue on a screen. In the example in FIG. 1, the interface feature 116 anchors the needle guidance device 106 on each end of the treatment site, although the needle guidance device 106 may also be anchored only on one side of the treatment site. In addition to the alternatives set forth above for the anchoring feature, the interface feature 116 also may be, for example, a button, sutures, both button and suture, or some other type of anchoring feature.

Figure 2:
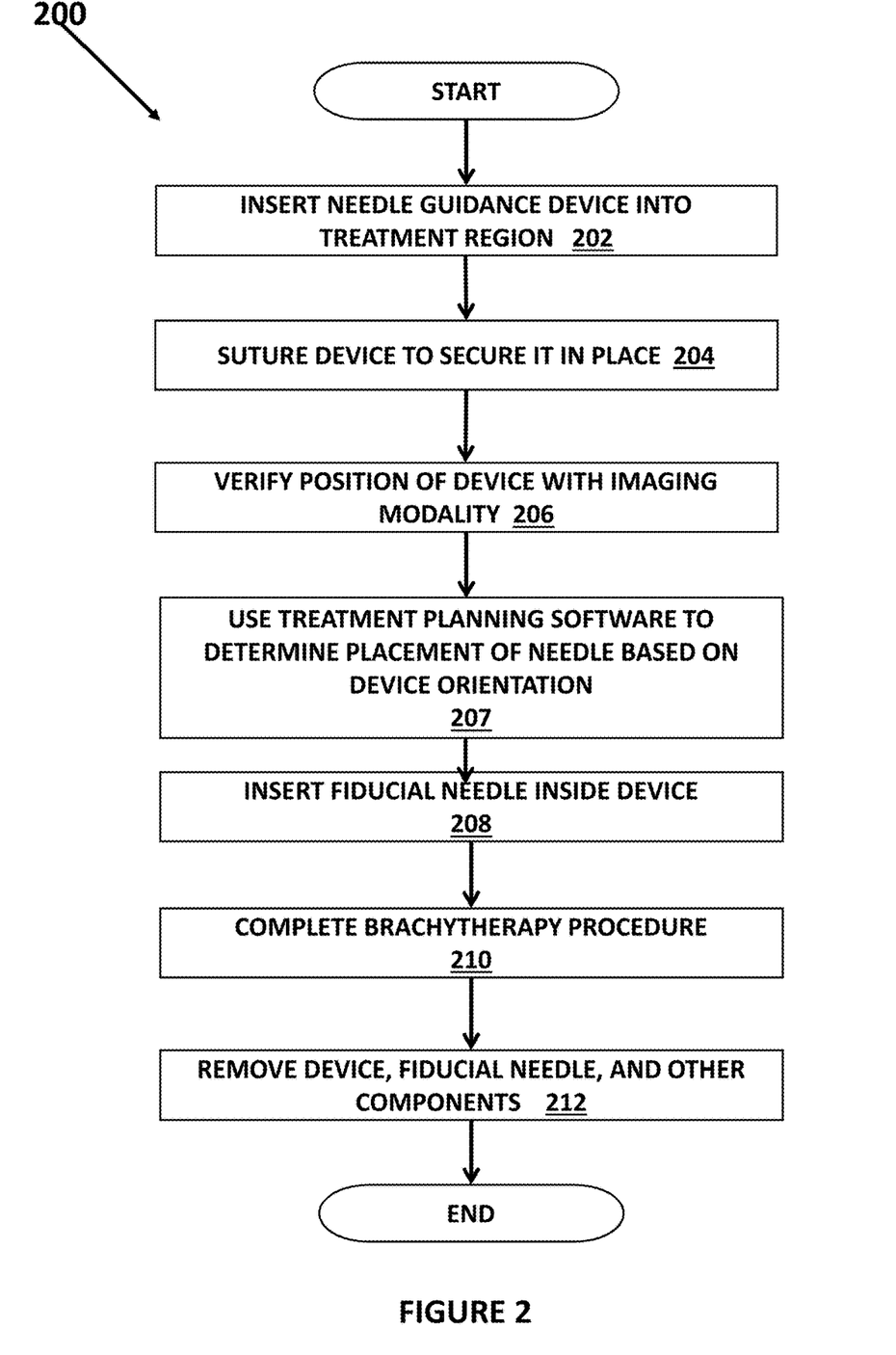
FIG. 2 illustrates a method of using the needle guidance device shown in FIG. 1.

FIG. 2 illustrates a method 200 of using the needle guidance device shown in FIG. 1. In one example, the needle guidance device is used to place one or more brachytherapy seeds into a treatment region which is a lumpectomy cavity in breast tissue from which a tumor was surgically removed previously. In a brachytherapy procedure in which one or more radioactive seeds are placed into the treatment region, one or more fiducial needles are first fixated into the treatment region through a brachytherapy template and then needles with the one or more radioactive seeds are inserted through the template (fixated by at least one fiducial needle) to place the one or more radioactive seeds precisely into the treatment region based on a treatment plan. The installed one or more radioactive seeds release radiation that irradiates the tissue in the treatment region. In one embodiment, the one or more radioactive seeds kill tumor cells in the lumpectomy region that remain after surgery to remove a tumor.

In the method, the needle guidance device 106, in the form of a cannula in one embodiment, is placed at the time of lumpectomy in the treatment region that is the lumpectomy cavity (202). The needle guidance device 106 may be secured in the lumpectomy cavity with sutures (204) to prevent migration. When the patient is confirmed to receive permanent breast seed implantation, a CT-visible marker is placed inside the device for treatment planning. The CT-visible marker has bands spaced 1 cm apart for depth measurements. Treatment planning (using treatment planning software) is done using the device as a reference point (206). During the treatment planning, the need guidance device is imaged and the treatment planning software (207) is used to plan one or more characteristics of the insertion of a brachytherapy needle, such as placement, angle and/or depth of insertion) prior to the procedure. The CT-visible marker is removed after the plan.

On the day of the radioactive seed implantation (that may be the same day/same time as the treatment planning or at a different time), a template grid of the brachytherapy fiducial needle fixation system (an example of which is described in U.S. Pat. No. 8,764,619 that is incorporated herein by reference) is set up. A fiducial needle may then be placed through the grid and inside the needle guidance device 106 (208) without the need for ultrasound guidance since the implanted needle guidance device 106 precisely guides the needles. The radioactive seeds may then be implanted per the treatment plan (210). Ultrasound guidance can be used for verification of the final placement of the radioactive seeds. The needle guidance device 106, the fiducial needles and other components then may be removed after the completion of the procedure (212).

In an alternative method, when the patient is confirmed to receive permanent breast seed implantation, the needle guidance device 106 may be placed percutaneously with a trochar. The device is visible under CT and ultrasound imaging. In this embodiment, the needle guidance device 106 may be secured in the lumpectomy cavity with an inflated balloon. Treatment planning is done using the device as a reference point. On the day of the implantation, the fiducial needle uses the guidewire component of the device as a track into the cavity without ultrasound guidance. Ultrasound guidance can be used for verification of the final placement. The device is removed after the completion of the procedure.

Figure 3:
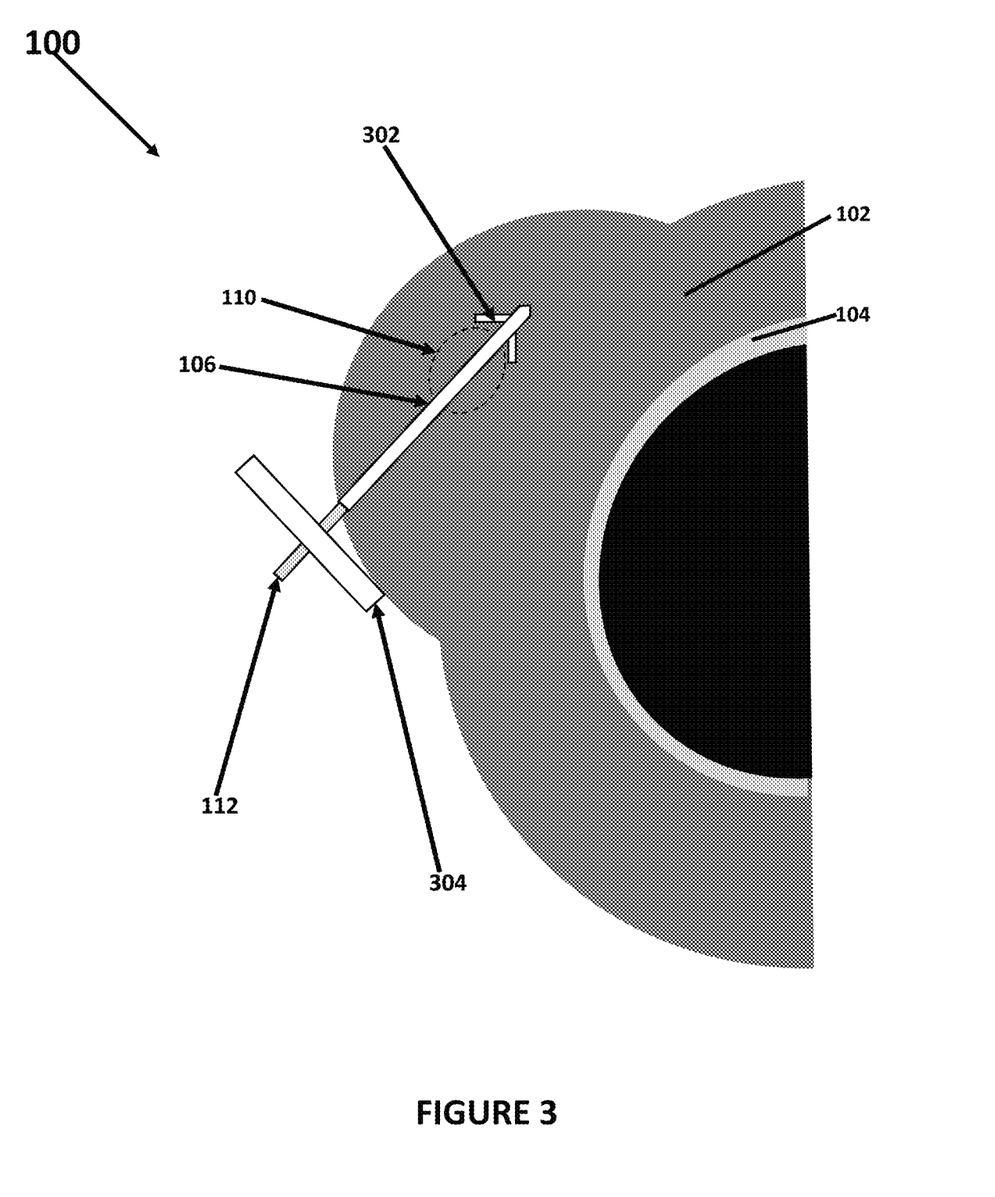
FIG. 3 is a caudal cross section of breast tissue and illustrates another example of the needle guidance device used with a brachytherapy fiducial needle fixation system.

FIG. 3 is a caudal cross section of breast tissue and illustrates another example of the needle guidance device 106 used with a brachytherapy fiducial needle fixation system. In this embodiment, many of the elements in FIG. 1 are the same and are labeled as such and will not be further described for this embodiment. In this embodiment, the needle guidance device 106 may have one or more deployable hooks 302 that may be the anchor device used to anchor the installed needle guidance device 106 at the treatment region 110. In operation, the hook(s) may be withdrawn into a distal end of the needle guidance device 106 during installation and then be deployed as shown in FIG. 3 once the needle guidance device 106 is placed adjacent/in the treatment region 110. Each hook may be spring biased so that it deploys once released. The hooks 302 may also use the same spring mechanism or a different spring mechanism to retreat the hooks for removal of the device. The needle guidance device 106 may also have a brachytherapy needle template guide 304 that is attached to the needle guidance device 106 as shown. The needle template guide 304 is a template through which fiducial needles and/or radioactive seed/source needles are guided into the treatment site in order to place one or more radioactive seeds/sources into/adjacent the treatment site.

Figure 4:
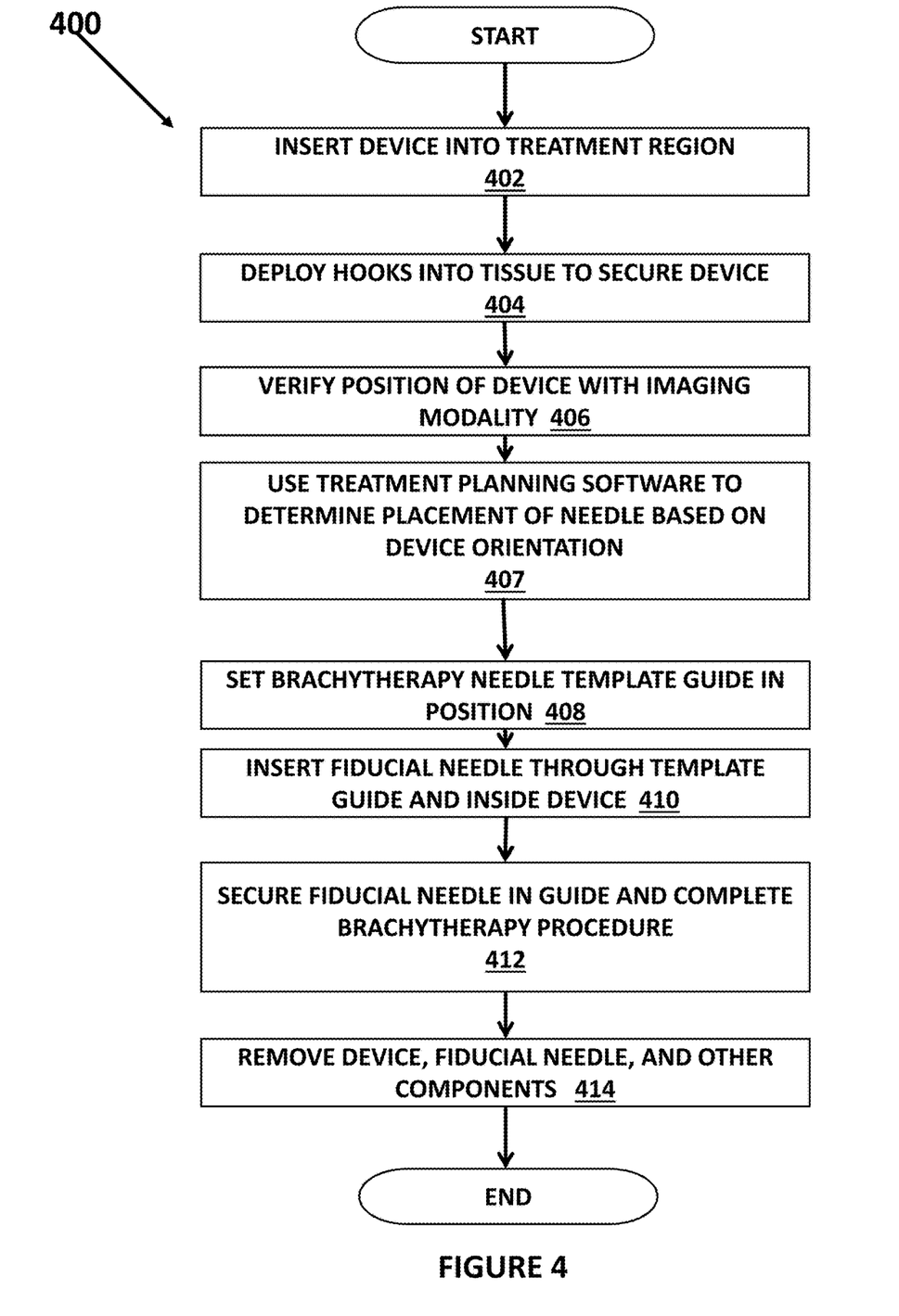
FIG. 4 illustrates another method of using the needle guidance device shown in FIG. 3.

FIG. 4 illustrates another method 400 of using the needle guidance device shown in FIG. 3. In one example, the needle guidance device is used to place one or more brachytherapy seeds into a treatment region which is a lumpectomy cavity in breast tissue from which a tumor was surgically removed previously. In the method, the needle guidance device 106, in the form of a cannula in one embodiment, is placed at the time of lumpectomy in the treatment region that is the lumpectomy cavity (402). The needle guidance device 106 may be secured in the lumpectomy cavity using the deployed hooks (404) to prevent migration. When the patient is confirmed to receive permanent breast seed implantation, a CT-visible marker is placed inside the device for treatment planning. The CT-visible marker has bands spaced 1 cm apart for depth measurements. Treatment planning (with known treatment planning software) is done using the device as a reference point (406). During the treatment planning, the need guidance device is imaged and the treatment planning software (407) is used to plan one or more characteristics of the insertion of a brachytherapy needle, such as placement, angle and/or depth of insertion) prior to the procedure. The CT-visible marker may be removed after the plan.

On the day of the radioactive seed implantation (that may be the same day/same time as the treatment planning or at a different time), a template grid of the brachytherapy fiducial needle fixation system (an example of which is described in U.S. Pat. No. 8,764,619 that is incorporated herein by reference) is set up and placed into position (408). Then, a fiducial needle may be placed through the grid and inside the needle guidance device 106 (410) and secured without the need for ultrasound guidance since the implanted needle guidance device 106 precisely guides the needles. The radioactive seeds may then be implanted per the treatment plan (412). Ultrasound guidance can be used for verification of the final placement of the radioactive seeds. The needle guidance device 106, the fiducial needles and other components then may be removed after the completion of the procedure (412).

In an alternative embodiment, the needle guidance device 106 may be a catheter that is open at both ends (unlike the embodiment shown in FIG. 1) that is inserted inside the body with a trocar which is the element that penetrates the tissue. Once the device 106 is inserted percutaneously inside the body, the trocar is removed. The device 106 may be anchored in place with a button at the skin surface. A brachytherapy needle is inserted inside the device for the placement of one or more radioactive seeds inside the body. The brachytherapy needle is removed and a fiducial needle is inserted inside so that it can be fixated with a brachytherapy needle template grid. The other brachytherapy needles can be inserted with the brachytherapy needle template grid.

The foregoing description, for purpose of explanation, has been described with reference to specific embodiments. However, the illustrative discussions above are not intended to be exhaustive or to limit the disclosure to the precise forms disclosed. Many modifications and variations are possible in view of the above teachings. The embodiments were chosen and described in order to best explain the principles of the disclosure and its practical applications, to thereby enable others skilled in the art to best utilize the disclosure and various embodiments with various modifications as are suited to the particular use contemplated.

The system and method disclosed herein may be implemented via one or more components, systems, servers, appliances, other subcomponents, or distributed between such elements. When implemented as a system, such systems may include an/or involve, inter alia, components such as software modules, general-purpose CPU, RAM, etc. found in general-purpose computers. In implementations where the innovations reside on a server, such a server may include or involve components such as CPU, RAM, etc., such as those found in general-purpose computers.

Additionally, the system and method herein may be achieved via implementations with disparate or entirely different software, hardware and/or firmware components, beyond that set forth above. With regard to such other components (e.g., software, processing components, etc.) and/or computer-readable media associated with or embodying the present inventions, for example, aspects of the innovations herein may be implemented consistent with numerous general purpose or special purpose computing systems or configurations. Various exemplary computing systems, environments, and/or configurations that may be suitable for use with the innovations herein may include, but are not limited to: software or other components within or embodied on personal computers, servers or server computing devices such as routing/connectivity components, handheld or laptop devices, multiprocessor systems, microprocessor-based systems, set top boxes, consumer electronic devices, network PCs, other existing computer platforms, distributed computing environments that include one or more of the above systems or devices, etc.

In some instances, aspects of the system and method may be achieved via or performed by logic and/or logic instructions including program modules, executed in association with such components or circuitry, for example. In general, program modules may include routines, programs, objects, components, data structures, etc. that perform particular tasks or implement particular instructions herein. The inventions may also be practiced in the context of distributed software, computer, or circuit settings where circuitry is connected via communication buses, circuitry or links. In distributed settings, control/instructions may occur from both local and remote computer storage media including memory storage devices.

The software, circuitry and components herein may also include and/or utilize one or more type of computer readable media. Computer readable media can be any available media that is resident on, associable with, or can be accessed by such circuits and/or computing components. By way of example, and not limitation, computer readable media may comprise computer storage media and communication media. Computer storage media includes volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical storage, magnetic tape, magnetic disk storage or other magnetic storage devices, or any other medium which can be used to store the desired information and can accessed by computing component. Communication media may comprise computer readable instructions, data structures, program modules and/or other components. Further, communication media may include wired media such as a wired network or direct-wired connection, however no media of any such type herein includes transitory media. Combinations of the any of the above are also included within the scope of computer readable media.

In the present description, the terms component, module, device, etc. may refer to any type of logical or functional software elements, circuits, blocks and/or processes that may be implemented in a variety of ways. For example, the functions of various circuits and/or blocks can be combined with one another into any other number of modules. Each module may even be implemented as a software program stored on a tangible memory (e.g., random access memory, read only memory, CD-ROM memory, hard disk drive, etc.) to be read by a central processing unit to implement the functions of the innovations herein. Or, the modules can comprise programming instructions transmitted to a general purpose computer or to processing/graphics hardware via a transmission carrier wave. Also, the modules can be implemented as hardware logic circuitry implementing the functions encompassed by the innovations herein. Finally, the modules can be implemented using special purpose instructions (SIMD instructions), field programmable logic arrays or any mix thereof which provides the desired level performance and cost.

As disclosed herein, features consistent with the disclosure may be implemented via computer-hardware, software and/or firmware. For example, the systems and methods disclosed herein may be embodied in various forms including, for example, a data processor, such as a computer that also includes a database, digital electronic circuitry, firmware, software, or in combinations of them. Further, while some of the disclosed implementations describe specific hardware components, systems and methods consistent with the innovations herein may be implemented with any combination of hardware, software and/or firmware. Moreover, the above-noted features and other aspects and principles of the innovations herein may be implemented in various environments. Such environments and related applications may be specially constructed for performing the various routines, processes and/or operations according to the invention or they may include a general-purpose computer or computing platform selectively activated or reconfigured by code to provide the necessary functionality. The processes disclosed herein are not inherently related to any particular computer, network, architecture, environment, or other apparatus, and may be implemented by a suitable combination of hardware, software, and/or firmware. For example, various general-purpose machines may be used with programs written in accordance with teachings of the invention, or it may be more convenient to construct a specialized apparatus or system to perform the required methods and techniques.

Aspects of the method and system described herein, such as the logic, may also be implemented as functionality programmed into any of a variety of circuitry, including programmable logic devices ("PLDs"), such as field programmable gate arrays ("FPGAs"), programmable array logic ("PAL") devices, electrically programmable logic and memory devices and standard cell-based devices, as well as application specific integrated circuits. Some other possibilities for implementing aspects include: memory devices, microcontrollers with memory (such as EEPROM), embedded microprocessors, firmware, software, etc. Furthermore, aspects may be embodied in microprocessors having software-based circuit emulation, discrete logic (sequential and combinatorial), custom devices, fuzzy (neural) logic, quantum devices, and hybrids of any of the above device types. The underlying device technologies may be provided in a variety of component types, e.g., metal-oxide semiconductor field-effect transistor ("MOSFET") technologies like complementary metal-oxide semiconductor ("CMOS"), bipolar technologies like emitter-coupled logic ("ECL"), polymer technologies (e.g., silicon-conjugated polymer and metal-conjugated polymer-metal structures), mixed analog and digital, and so on.

It should also be noted that the various logic and/or functions disclosed herein may be enabled using any number of combinations of hardware, firmware, and/or as data and/or instructions embodied in various machine-readable or computer-readable media, in terms of their behavioral, register transfer, logic component, and/or other characteristics. Computer-readable media in which such formatted data and/or instructions may be embodied include, but are not limited to, non-volatile storage media in various forms (e.g., optical, magnetic or semiconductor storage media) though again does not include transitory media. Unless the context clearly requires otherwise, throughout the description, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list and any combination of the items in the list.

Although certain presently preferred implementations of the invention have been specifically described herein, it will be apparent to those skilled in the art to which the invention pertains that variations and modifications of the various implementations shown and described herein may be made without departing from the spirit and scope of the invention. Accordingly, it is intended that the invention be limited only to the extent required by the applicable rules of law.

While the foregoing has been with reference to a particular embodiment of the disclosure, it will be appreciated by those skilled in the art that changes in this embodiment may be made without departing from the principles and spirit of the disclosure, the scope of which is defined by the appended claims

What is claimed is:

1. A brachytherapy needle guidance device, comprising:
a body portion being a hollow tube and having a distal end and a proximal end;

an anchoring feature that is capable of anchoring the brachytherapy needle guidance device into tissue;

an imaging feature that is capable of being used by a treatment planning software;

a feature at the distal end of the body portion that is capable of penetrating the tissue in order to insert the brachytherapy needle guidance device into the tissue;

a brachytherapy template attached to the proximal end of the body portion; and wherein a brachytherapy needle is capable of being inserted through the hollow tube and guided into the tissue once the brachytherapy needle guidance device is anchored in the tissue.

2. The device of claim 1, wherein the anchoring feature is one of a set of holes for suturing, a set of hooks, a button, and an inflatable balloon.

3. The device of claim 1, wherein the feature that is capable of penetrating the tissue further comprises one of a sharpened tip at a distal end of the body portion and a trocar with an open end.

4. The device of claim 1, wherein the body portion further comprises one of a guidewire that can be used with a hollow needle and a balloon catheter.

5. A brachytherapy needle guidance device, comprising:
a body portion being a hollow tube and having a distal end and a proximal end;

an anchoring feature that is capable of anchoring the brachytherapy needle guidance device into tissue;

an imaging feature that is capable of being used by a treatment planning software;

a feature at the distal end of the body portion that is capable of penetrating the tissue in order to insert the brachytherapy needle guidance device into the tissue;

wherein the feature that is capable of penetrating the tissue further comprises one of a sharpened tip at a distal end of the body portion and a trocar with an open end and the body portion is a catheter that is capable of being inserted into the tissue using the trocar; and wherein a brachytherapy needle is capable of being inserted through the hollow tube and guided into the tissue once the brachytherapy needle guidance device is anchored in the tissue.

6. A method for guiding a brachytherapy needle, the method comprising:
providing a needle guidance device being a hollow tube and having a body portion having a distal end and a proximal end, an anchoring feature that is capable of anchoring the needle guidance device into tissue and a feature at the distal end of the body portion that is capable of penetrating the tissue in order to insert the needle guidance device into the tissue;

imaging the needle guidance device and using a treatment planning software to plan a set of characteristics of insertion of a brachytherapy needle into the treatment region;

inserting the needle guidance device into a treatment region in the tissue;

anchoring, by the anchoring feature of the needle guidance device, the needle guidance device at the treatment region;

attaching a brachytherapy template to the proximal end of the body portion; and inserting a brachytherapy needle through the hollow tube and the brachytherapy template into the treatment region.

7. The method of claim 6, wherein providing the needle guidance anchoring feature further comprises providing one of a set of holes for suturing, a set of hooks and an inflatable balloon.

8. The method of claim 6, wherein providing the needle guidance device that is capable of penetrating the tissue further comprises providing one of a sharpened tip at a distal end of the body portion and a trocar with an open end.

9. The method of claim 6, wherein providing the needle guidance device further comprises providing one of a guidewire that can be used with a hollow needle and a balloon catheter.

10. A brachytherapy treatment method using needle guidance, the method comprising:
installing a needle guidance device into a treatment region in a tissue, the needle guidance device being a hollow tube;

anchoring the needle guidance device at the treatment region;

imaging the needle guidance device for use with a treatment planning software to plan a set of characteristics for an insertion of the brachytherapy device into the treatment region;

inserting a brachytherapy device through the hollow tube of the needle guidance device without imaging into the treatment region;

attaching a brachytherapy template onto the needle guidance device and wherein inserting the brachytherapy device further comprises inserting the brachytherapy device through the brachytherapy template into the treatment region; and placing one or more radioactive seeds into the treatment region.

11. The method of 10, wherein the brachytherapy device further comprises a brachytherapy fiducial needle.

12. The method of claim 10, wherein installing the needle guidance device further comprises penetrating the tissue using a sharpened tip at a distal end of the needle guidance device.

13. The method of claim 10, wherein installing the needle guidance device further comprises using a trocar to install the needle guidance device.

14. The method of claim 13, wherein installing the needle guidance device further comprises inserting a catheter into the tissue using the trocar.

15. The method of claim 10, wherein anchoring the needle guidance device further comprises suturing the needle guidance device once installed into the treatment region.

16. The method of claim 10, wherein anchoring the needle guidance device further comprises deploying one or more hooks once installed into the treatment region.

17. The method of claim 10, wherein placing one or more radioactive seeds into the treatment region further comprises placing the one or more radioactive seeds into a lumpectomy cavity in breast tissue.

* * * * *